US008623803B2

(12) United States Patent
Gelin

(10) Patent No.: US 8,623,803 B2
(45) Date of Patent: *Jan. 7, 2014

(54) CHILDREN'S HYGIENE PRODUCTS SHAPED LIKE SPORTS BALLS

(76) Inventor: Marie C. Gelin, Fairburn, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/164,110

(22) Filed: Jun. 20, 2011

(65) Prior Publication Data

US 2011/0244009 A1    Oct. 6, 2011

Related U.S. Application Data

(63) Continuation-in-part of application No. 12/434,624, filed on May 2, 2009, now abandoned.

(51) Int. Cl.
*A61K 8/00* (2006.01)

(52) U.S. Cl.
USPC ............ 510/141; 510/142; 510/148; 510/152

(58) Field of Classification Search
USPC ......................................................... 510/141
See application file for complete search history.

(56) References Cited

U.S. PATENT DOCUMENTS

| 606,024 | A | | 6/1898 | Peraglie |
|---|---|---|---|---|
| 1,416,962 | A | | 5/1922 | Meeks |
| 1,636,709 | A | | 7/1927 | Schmidt |
| 1,787,660 | A | | 1/1929 | Blakeley |
| 2,099,484 | A | * | 11/1937 | Hokerk ........................ 248/686 |
| 2,182,893 | A | | 8/1938 | Hokerk |
| 2,243,634 | A | | 11/1939 | Kadish |
| 2,182,293 | A | | 12/1939 | Hokerk |
| 2,883,791 | A | | 5/1958 | Ballo |
| 3,160,523 | A | | 12/1964 | Hull |
| 3,206,152 | A | | 9/1965 | Wimmer |
| 3,251,571 | A | | 5/1966 | Ernest |
| 3,341,457 | A | | 9/1967 | Schmidt |
| 3,519,568 | A | | 7/1970 | Needleman |
| 3,693,923 | A | | 9/1972 | Ayoub |
| 3,796,665 | A | | 3/1974 | Allen |
| D259,064 | S | | 4/1981 | Lee |
| D379,249 | S | | 5/1997 | Williams |
| D384,438 | S | | 9/1997 | Hage |
| D405,926 | S | | 2/1999 | Badillo |

(Continued)

OTHER PUBLICATIONS

File History of parent U.S. Appl. No. 12/434,624 including Office Action mailed Dec. 14, 2010 and response thereto filed Jun. 14, 2011.

(Continued)

*Primary Examiner* — Necholus Ogden, Jr.
(74) *Attorney, Agent, or Firm* — Robert A. Seldon

(57) ABSTRACT

A child's hygienic product comprises a body of hygiene material having an exterior surface simulating a sports ball that is sized to fit the palm of a child's hand. The hygiene material's body has a through hole communicating with the exterior surface at spatially separated regions. A portion of a generally looped shaped cord or band of resiliently stretchable material is positioned within the through-hole, and the portion emerging from the spatially separated regions extends around the outside surface of the hygiene material's body in close proximity thereto. The band is sized to extend around the hand of the child when the hygiene material's body is held by the child to generally secure the hygiene material's body in a position adjacent the child's palm when the child is using the product.

12 Claims, 4 Drawing Sheets

(56) References Cited

U.S. PATENT DOCUMENTS

| | | |
|---|---|---|
| 5,895,780 A | 4/1999 | Tokosh et al. |
| 6,136,764 A | 10/2000 | Bitton |
| 6,190,079 B1 | 2/2001 | Ruff |
| 6,455,478 B1 | 9/2002 | Bitton |
| 6,720,296 B1 | 4/2004 | Bitton |
| 6,799,917 B1 | 10/2004 | Sampson |

OTHER PUBLICATIONS http://www.soapshapes.com/SScart/products.php?cat=20.

* cited by examiner

US 8,623,803 B2

CHILDREN'S HYGIENE PRODUCTS SHAPED LIKE SPORTS BALLS

CROSS-REFERENCE TO RELATED APPLICATIONS

This is a continuation in part of U.S. patent application Ser. No. 12/434,624 filed May 2, 2009, the priority of which is claimed, and the content of which is hereby incorporated by reference.

BACKGROUND OF THE INVENTION

The present invention relates to hygiene products and particularly to skin-contacting hygiene products for children such as soap, shampoo, combination soap/shampoo, body lotion, and deodorant.

Today, many young boys and girls spend much of their time playing their favorite sports. While they are highly involved and developing skills and agility and strength, they get pretty smelly and are not always interested in hygiene. This, as known to many parents, is particularly true of young boys, and the battle to get kids to take a meaningful bath or shower is one of the most universal experiences of parenthood.

Moreover, there are many hygiene products for adults which contain ingredients that are too strong, harsh or unpleasant in smell for children and teenagers. Adult hygiene products are often sized, shaped and scented inappropriately for children and teenagers and may not be easy to handle and use. Boys in particular are not very interested in products which they consider unmasculine or boring adult products.

BRIEF SUMMARY OF THE INVENTION

A hygiene product for children comprises a skin-contacting body of hygiene material having an external surface simulating a sports ball and sized to fit a child's hand, together with a cord or band (hereinafter, collectively "band") of material sufficiently reversibly stretchable to enable the band to be slide over the child's knuckles and yet sufficiently secure the ball adjacent the child's palm when the product is being used so that it is not dropped.

The band is preferably a closed loop, a portion of which is embedded within the body of hygiene material. The preferred configuration accordingly provides a band-accommodating through-hole within the body of hygienic material that enables the band to emerge from opposite sides of the body at positions that discourage the band from being pulled through the body during the life of the product. Moreover, any force exerted on the band during its mounting to, and removal from, the child's hand is distributed along the embedded length of the band, thereby minimizing the pressure (i.e., force per unit of area) exerted by the band against the body of hygiene material when the band is being mounted on, secured on or removed from the child's hand.

The content of parent U.S. patent application Ser. No. 12/434,624 filed May 2, 2009 (published on Nov. 4, 2010 as U.S. Patent Application 20100279907) is hereby incorporated by reference.

These and other details of my invention will be described in connection with the accompanying drawings, which are furnished only by way of illustration and not in limitation of the invention, and in which drawings:

DETAILED DESCRIPTION OF THE PREFERRED EMBODIMENT

Figure 1:
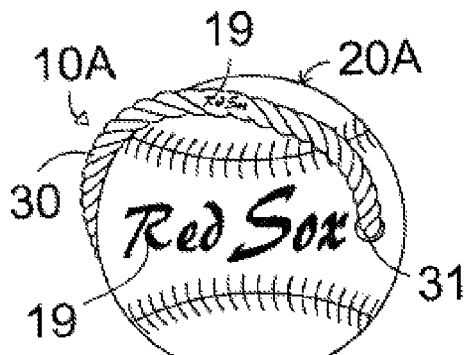
FIG. 1 is a perspective view of a hygiene product constructed in accordance with the invention and showing the hygiene material body synthesizing a baseball.
Figure 2:
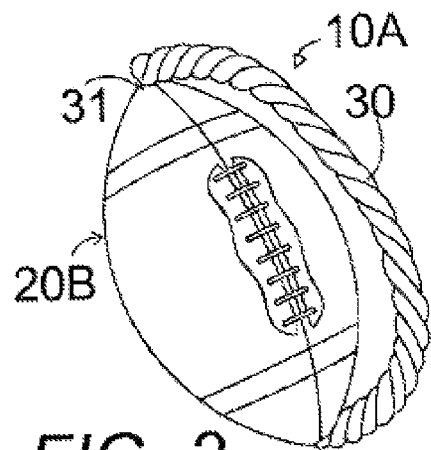
FIG. 2 is a perspective view of a hygiene product constructed in accordance with the invention and showing the hygiene material body synthesizing a football.
Figure 3:
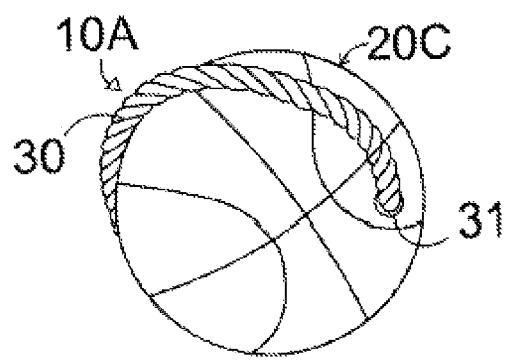
FIG. 3 is a perspective view of a hygiene product constructed in accordance with the invention and showing the hygiene material body synthesizing a basketball.
Figure 4:
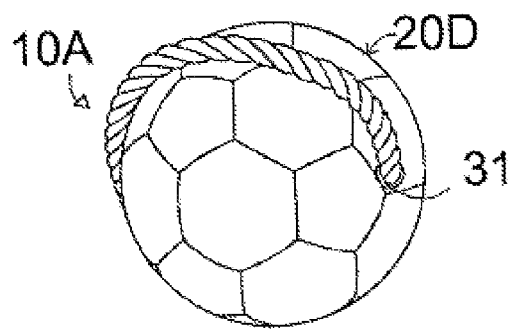
FIG. 4 is a perspective view of a hygiene product constructed in accordance with the invention and showing the hygiene material body synthesizing a soccer ball.
Figure 5:
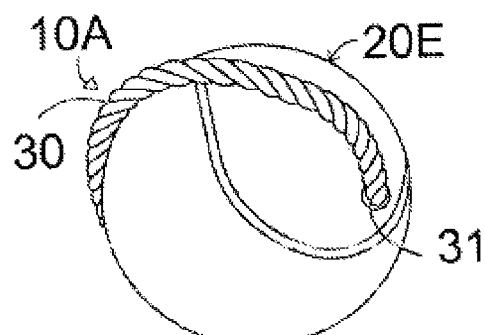
FIG. 5 is a perspective view of a hygiene product constructed in accordance with the invention and showing the hygiene material body synthesizing a tennis ball.
Figure 6:
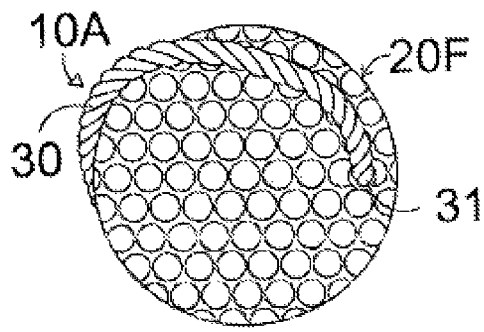
FIG. 6 is a perspective view of a hygiene product constructed in accordance with the invention and showing the hygiene material body synthesizing a golf ball.
Figure 7:
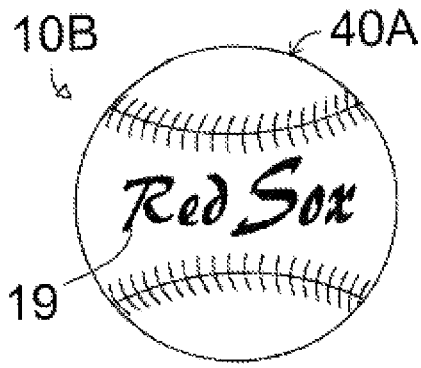
FIG. 7 is a perspective view of a hygiene product constructed in accordance with the invention and showing butterball lotion hygiene material synthesizing a baseball and having a team insignia on the ball.
Figure 8:
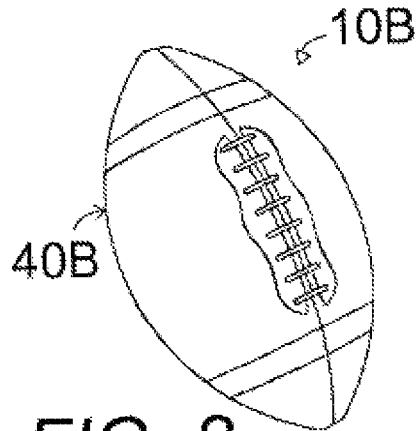
FIG. 8 is a perspective view of a hygiene product constructed in accordance with the invention and showing butterball lotion hygiene material synthesizing a football.
Figure 9:
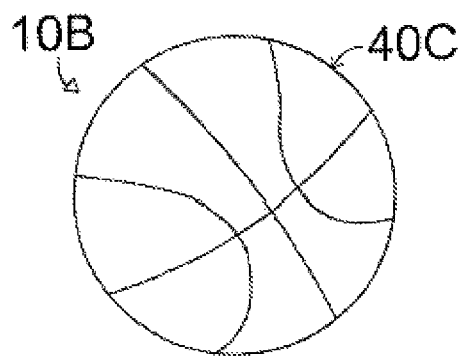
FIG. 9 is a perspective view of a hygiene product constructed in accordance with the invention and showing butterball lotion hygiene material synthesizing a basketball.
Figure 10:
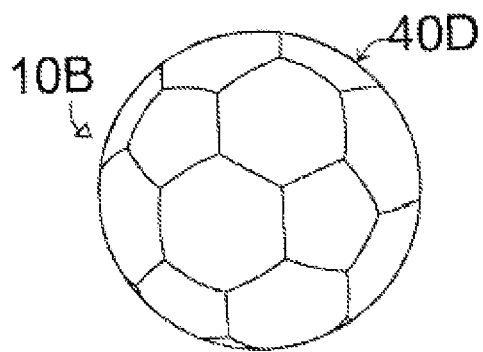
FIG. 10 is a perspective view of a hygiene product constructed in accordance with the invention and showing butterball lotion hygiene material synthesizing a soccer ball.
Figure 11:
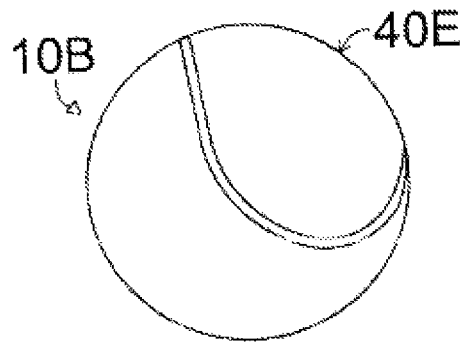
FIG. 11 is a perspective view of a hygiene product constructed in accordance with the invention and showing butterball lotion hygiene material synthesizing a tennis ball.
Figure 12:
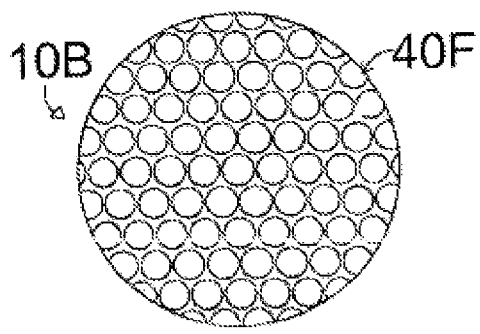
FIG. 12 is a perspective view of a hygiene product constructed in accordance with the invention and showing butterball lotion hygiene material synthesizing a golf ball.

FIGS. 1-6 are perspective views of a hygiene product constructed in accordance with the invention and respectively showing the hygiene material body 20A-F synthesizing a baseball, a football, a basketball, a soccer ball, a tennis ball and a golf ball. It will be clear to those of ordinary skill in the art that other sports balls are within the scope of the invention.

The hygiene material body is formed from a soap, shampoo, soap/shampoo combination or generally solidified body lotion composition, and has an exterior surface that simulates the shape and visual characteristics of the sports ball it emulates. The hygiene material body 20A-20F is sized to fit in a child's hand for applying the hygiene material to the child's body.

The preferred hygiene material accordingly contains non-caustic mild skin soothing ingredients for use on a child's body to sooth and not irritate the child's sensitive skin, and contains a mild scent less strong than adult scented hygiene products so that the scent is aromatically soothing and not overpowering to the child's sense of smell. The fragrance is preferably non-flowery scent appealing to a young boy when the product is aimed a that market segment. Preferably, the hygiene material contains a mixture of naturally occurring mild-to-the-skin ingredients (preferably organic) rather than harsh synthetic ingredients.

The hygiene material is preferably molded in the shape of the simulated sports ball 20A-20F to impart the desired design topography to the simulated sports ball. The mold is preferably configured to provide a through-hole 31 through the simulated sports ball's body that communicates with the exterior surface of the body at generally diametrically opposite regions.

An elasticized cord loop 30 passes through the through-hole, and extends around an outside surface of the simulated sports ball in close proximity thereto. The cord loop is sized to pass behind the child's hand when the hygiene material body is placed on or adjacent to the child's palm to generally help secure the hygiene material's body in the child's palm when the child is using the product, and generally prevent the child from dropping the hygiene material.

The cord is sufficiently elastic to permit it to pass over the child's knuckles as the hand is inserted through the space between the hygiene material and cord. The force exerted by the cord against the hygiene material during the insertion is dissipated along the embedded length of the cord, and is therefore less likely to move towards the outer surface of the hygiene material as a result of any forces arising from the passing of the cord over the child's knuckles, particularly in view of the degree of elasticity provided to the cord. The preferred emergence of the loop from diametrically opposite regions of the hygiene material's body maximizes the embedded length of cord over which the force is dissipated. Naturally, a lesser embedded length can be provided.

Those skilled in the art will recognize that the through-hole may be formed by the cord itself rather than a machining or similar operation. For example, one half of hygiene material's body may be poured into a mold that gives the body its sports ball-simulating exterior surface, the portion of the band to be embedded in the body is then laid on top of the material, and a second mold of material forming the other half of the ball (or a quantity of molded material forming the other half of the ball) can then be brought into contact with the first half of the ball and cord to secure the cord therebetween and to complete formation of the ball.

The through-hole can alternatively be predefined by the mold or molds into which the hygiene material is placed for shaping and appropriate surface topography. For example, two hemispheres of a round ball can be separately molded, with each having a generally curved region extending across its diameter that will form its half of the through hole's wall when joined with a second hemisphere defining the other half of the through-hole wall. The portion of the cord to be embedded is the laid along the generally curved region, and the material forming the second hemisphere is then overlaid to form the completed ball, the two hemisphere being sealed in place by an appropriate binder, heat or other techniques known by manufacturers of such products to be effective for that purpose.

Figure 13:
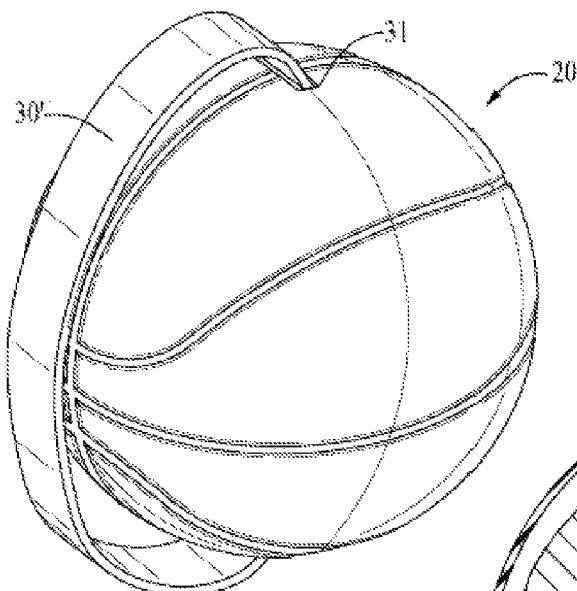
FIG. 13 is a perspective view of an alternative embodiment of a hygiene product constructed in accordance with the invention and having hygiene material body synthesizing a basketball.
Figure 15:
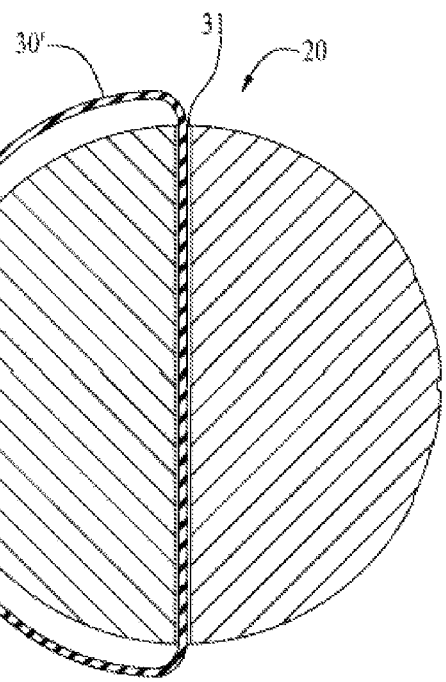
FIG. 15 is a cross-sectional view of the hygiene product taken along line 15-15 of FIG. 13.
Figure 14:
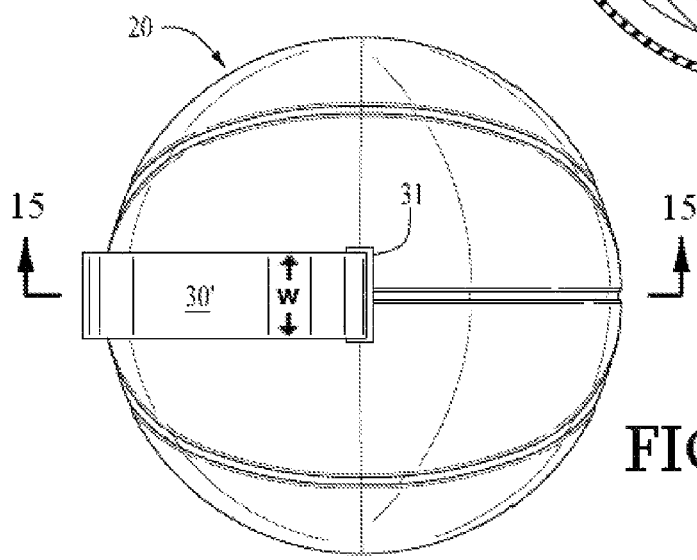
FIG. 14 is a top plan view of the hygiene product illustrated in FIG. 13.

An alternative embodiment of the invention is illustrated in FIGS. 13-15 wherein a band 30' is utilized instead of a cord. FIG. 13 is a perspective view of a hygiene product constructed in accordance with the invention wherein the hygiene material's body simulates a basketball, but it should be recognized that any other sports ball could be simulated without departing from the intended scope of the invention. FIG. 14 is a top plan view of the hygiene product illustrated in FIG. 13, while FIG. 15 is a cross-sectional view of the hygiene product illustrated in FIG. 13 taken along 15-15 of FIG. 14. In this embodiment, a resiliently stretchable band 30', preferably formed from a slightly stretchable silicone material, extends through a generally slot-shaped through-hole 31 formed through the hygiene material's body 20 in any of the same manners suggested above with respect to the cord. The band 30' extends around the outside surface of the hygiene body in close proximity to the outside surface of the simulated sports ball. The band is loop-shaped, as best shown in FIG. 15, and is sized to generally secure the hygiene material against or adjacent to the child's palm when the product is in use. In practice, a silicone band having a 700 mm diameter and a width w (FIG. 14) of 100 mm is embedded in a round body of hygiene material having a 900 mm diameter.

The band 30' has at least two advantages over the cord. First, it presents a flat surface against the body of hygiene material in the direction towards which it is pulled as the child's hand is inserted into the space between the hygiene material and band. This further minimizes the pressure ((i.e., force per unit of area) exerted against the hygiene material, further reducing the possibility that it will be pulled through the material during the hand-insertion or hand-removal steps. Second, the tactile sensation to the child is more akin to the strap of a baseball glove, further encouraging the child (especially baseball-worshipping boys) to use the product to get clean. Even better, the child may actually look forward to the bath or shower, knowing that (s)he will get to use the product.

Figure 16:
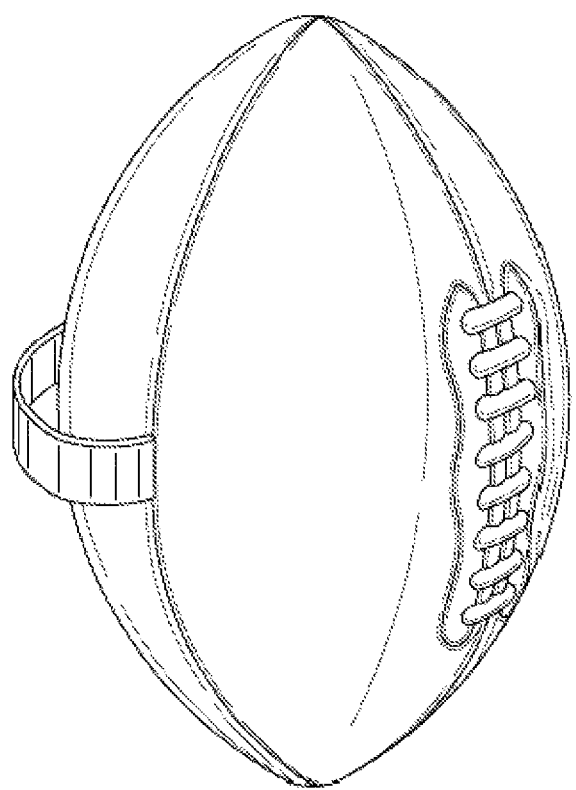
FIG. 16 is a perspective view of an alternative embodiment of a hygiene product constructed in accordance with the invention showing hygiene material synthesizing a football.
Figure 17:
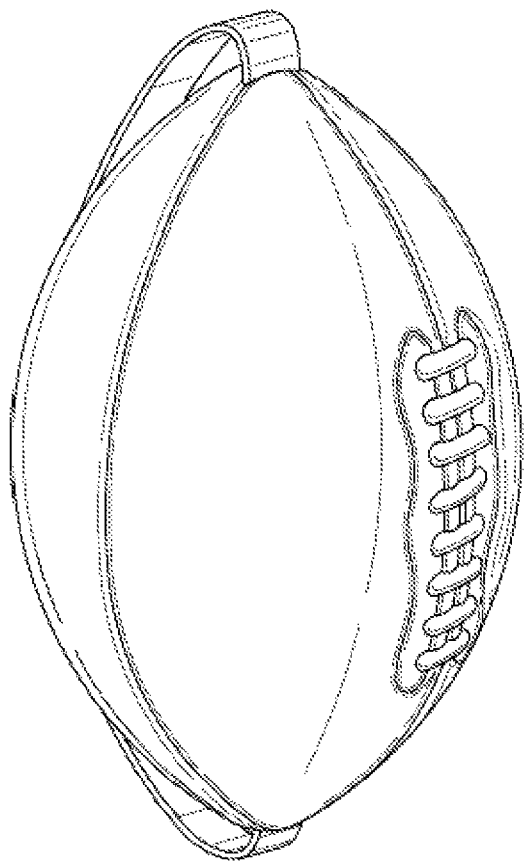
FIG. 17 is a perspective view of an alternative embodiment of the hygiene product of FIG. 16.

While most sports balls are round, and the preferred placement of diametrically opposite regions from which the band or cord emerges is unambiguous, there are some sports balls such as football and rugby balls that are generally ovoid in shape. Reference is made to FIGS. 16 and 17 which are perspective views of alternative embodiment of a hygiene product constructed in accordance with the invention when the simulated sports ball is generally ovoid. As illustrated in these Figures, the band (or cord) may emerge from diametrically opposite regions about a minor diameter of the ball (FIG. 16) or from diametrically opposite regions about a major diameter of the ball (FIG. 17). In both these Figures, the preferred position is shown as being on the largest major diameter and the largest minor diameter, since that positioning results in a centralized grip of the hygiene material by the child, and provides minimal pressure of the band against the hygiene material when the child's hand is inserted into or withdrawn from the space between the band and the soap. Of the two orientations, that shown in FIG. 17 is preferred because (assuming both simulated sports balls are the same size) it provides the child with a smaller (and therefore easier) curved surface to grip while, at the same time, providing maximum embedded length of the band-shaped loop to minimum the band's pressure against the hygiene material when the child's hand is being inserted into or withdrawn from the space between the band and the soap In FIGS. 7-12, the child's hygiene product 10B comprises a simulated sports ball 40A-40F comprising a skin soothing and moisturizing lotion containing natural skin soothing and moisturizing ingredients molded in the shape of a butterball lotion simulated sports ball 40A-40F sized to fit in a palm of a boy's hand. While the external surface of the product simulates the desired sports ball, no cord or band is necessary, and the product is accordingly illustrated without that feature.

The simulated sports ball 40A-40F of FIGS. 7-12 preferably comprises a solid lotions bar or deodorant.

It is understood that the preceding description is given merely by way of illustration and not in limitation of the invention, and that various modifications may be made thereto without departing from the spirit of the invention as claimed. It is accordingly intended that the invention be defined solely by the appended claims.

What is claimed is:

1. A child's hygienic product comprising:
   a body of hygiene material having an exterior shape and surface pattern simulating the shape and exterior pattern of a sports ball selected from the group consisting of a baseball, a football, a basketball, a soccer ball, a tennis ball and a golf ball, and sized to fit the palm of a child's hand;
   the hygiene material's body having a through hole communicating with the exterior surface at spatially separated regions; and
   a generally looped shaped cord or band of resiliently stretchable silicone material, a portion of which is positioned within the through-hole, and a portion of which emerges from the spatially separated regions and extends around the outside surface of the hygiene material's body in close proximity thereto, the cord or band being sized to extend around the hand of the child when the hygiene material's body is held by the child to generally secure the hygiene material's body in a position adjacent the child's palm when the child is using the product.

2. The hygienic product of claim 1 wherein the hygiene material's body is characterized by at least one diameter, and the spatially separated regions are at generally diametrically opposite regions of the body.

3. The product of claim 2 wherein the body of hygiene material is generally ovoid in shape, and the spatially-separated regions are at generally diametrically opposite regions of the body with respect to a major diameter of the ovoid.

4. The product of claim 2 wherein the body of hygiene material is generally ovoid in shape, and the spatially-separated regions are at generally diametrically opposite regions of the body with respect to a minor diameter of the ovoid.

5. The product of claim 1 wherein the cord or band is sufficiently stretchable to permit it to pass over the child's knuckles as the hand is inserted through the space defined between the hygiene material's body and the closely proximate cord or band.

6. The product of claim 1 wherein the body of hygiene material has a diameter of approximately 900 mm.

7. The product of claim 1 wherein the cord or band is a loop of approximately 700 mm in diameter.

8. The product of claim 1 wherein the cord or band has a width of approximately 100 mm.

9. A method for motivating a young child to take an effective bath or shower comprising the step of providing the child with a body of hygiene material having (a) an exterior surface simulating the shape and exterior pattern of a sports ball selected from the group consisting of a baseball, a football, a basketball, a soccer ball, a tennis ball and a golf ball, and sized to fit the palm of a child's hand, (b) a through-hole communicating with the exterior surface at spatially separated regions, and (c) a generally looped shaped cord or band of resiliently stretchable silicone material partially embedded within the body of hygiene material so that a portion of the cord or band emerges from spatially separated regions of the hygiene product body and extends around the outside surface of the hygiene material's body in close proximity thereto, the band being sized to extend around the hand of the child when the hygiene material's body is held by the child to generally secure the hygiene material's body in a position adjacent the child's palm when the child is using the product.

10. The method of claim 9 including the additional step of inserting the child's hand into the space between hygienic material's body and the closely proximate band or chord.

11. The product of claim 3 the spatially-separated regions are at generally diametrically opposite regions of the body with respect to the body's major diameter.

12. The product of claim 4 wherein the spatially-separated regions are at generally diametrically opposite regions of the body with respect to the body's minor diameter.

* * * * *